United States Patent

Plant Pat. 3,921
Patented June 22, 1976

3,921
IMPATIENS PLANT

Claude Hope and Rafael Angel Montoya Murillo, Cartago, Costa Rica, assignors to Goldsmith Seeds Inc., Gilroy, Calif.

Filed June 16, 1975, Ser. No. 587,381
Int. Cl. A01h *5/00*
U.S. Cl. Plt.—68 1 Claim

ABSTRACT OF THE DISCLOSURE

The present invention relates to a new and distinct cultivar of impatiens plant distinguished by large very double flowers of light pink color. It is a second generation seedling from a cross between the existing double clone "Appleblossom" and a light pink semi-double clone selected from single *Impatiens sultani.*

BACKGROUND OF THE INVENTION

The invention is concerned with the breeding of improved varieties of impatiens (*Impatiens sultant*). The prime object of the breeding was to produce a new impatiens cultivar with large very double flowers of a light pink color. The objective was substantially achieved along with other desirable improvements as evidenced by the following unique combinations of characteristics which are outstanding in the new cultivar and which distinguish it from its parents as well as from all other impatiens cultivars.

First, the plant is vigorous and heavily branched and grows in an upright but bushy manner. Second, the flowers of the plant are large compared to that of the plants from which it was bred. Third, the new cultivar exhibits a significantly larger number of whorls of petals over that of the existing double clone "Appleblossom" which was crossed to produce it. Fourth, the color of the flowers is light pink.

Asexual reproduction of this new cultivar by cuttings was performed at Cartago, Costa Rica and Gilroy, Calif. The new cultivar was selected from second generation self-pollinated progeny of the cross breeding of the existing double clone "Appleblossom" and a light pink semi-double clone selected from single *Impatiens sultani.* On asexual reproduction by cuttings, the new cultivar was found to retain its distinctive characteristics as listed herein through successive propagations.

BRIEF DESCRIPTION OF THE DRAWINGS

The invention will be better understood by reference to the figures of the drawings wherein.

DETAILED DESCRIPTION OF THE DRAWINGS

The following is a detailed description of the new impatiens plant of the present invention. The color terminology used in following is in accordance with the Royal Horticultural Society Colour Chart, except where ordinary dictionary significance of color is indicated.

The parentage of the new impatiens plant is as follows:

Seed parent—unnamed
Pollen parent—Appleblossom

The classification of the impatiens plant is as follows:

Botanical—*Impatiens sultani*

Pollen from Appleblossom was crossed with an unnamed light pink semi-double clone seed parent to produce a first generation. The best plants from the first generation were selected and self-pollinated to produce a second generation. The best plants from the second generation, in the sense of the plant having the most desired color, highest degree of doubleness, and largest size of flowers, was asexually reproduced by cuttings at Cartago, Costa Rica and Gilroy, Calif., U.S.A.

Figure 1:
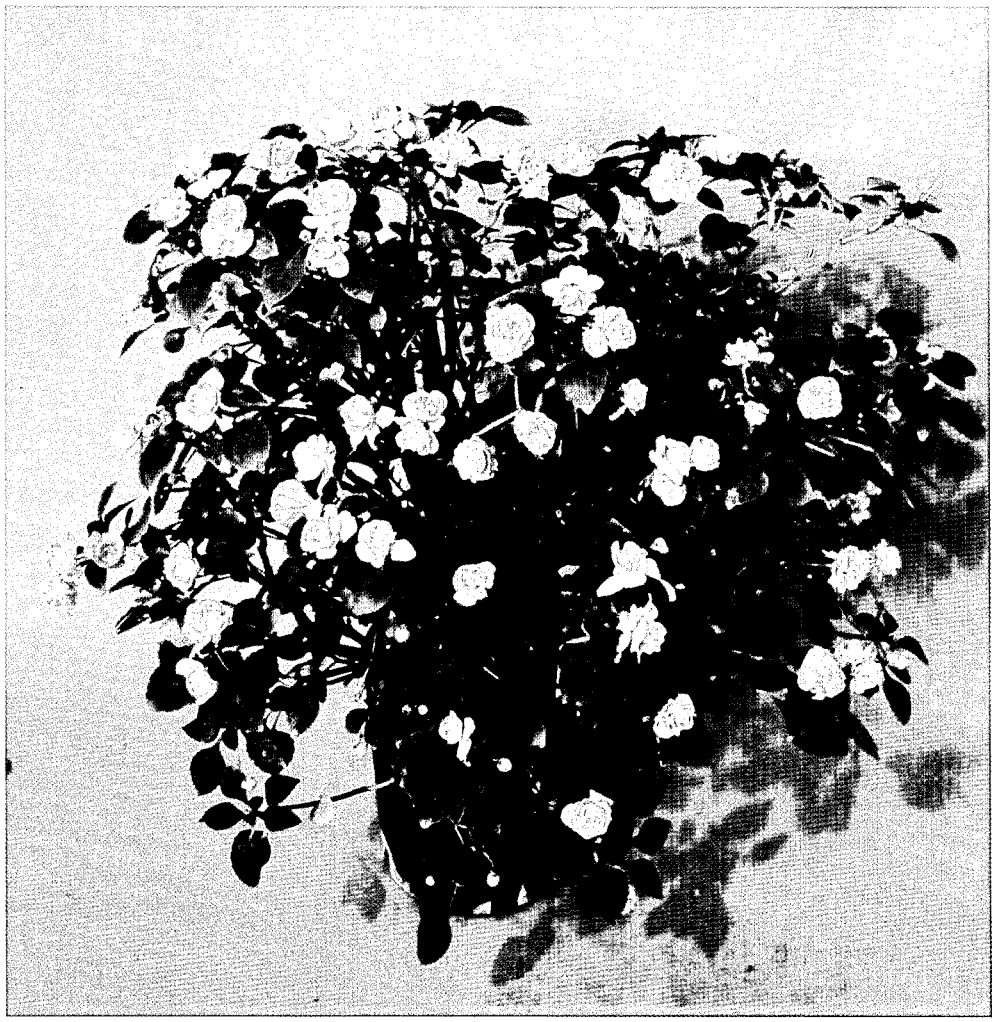
FIG. 1 is an overall view illustrating an impatiens plant of the present invention.
Figure 2:
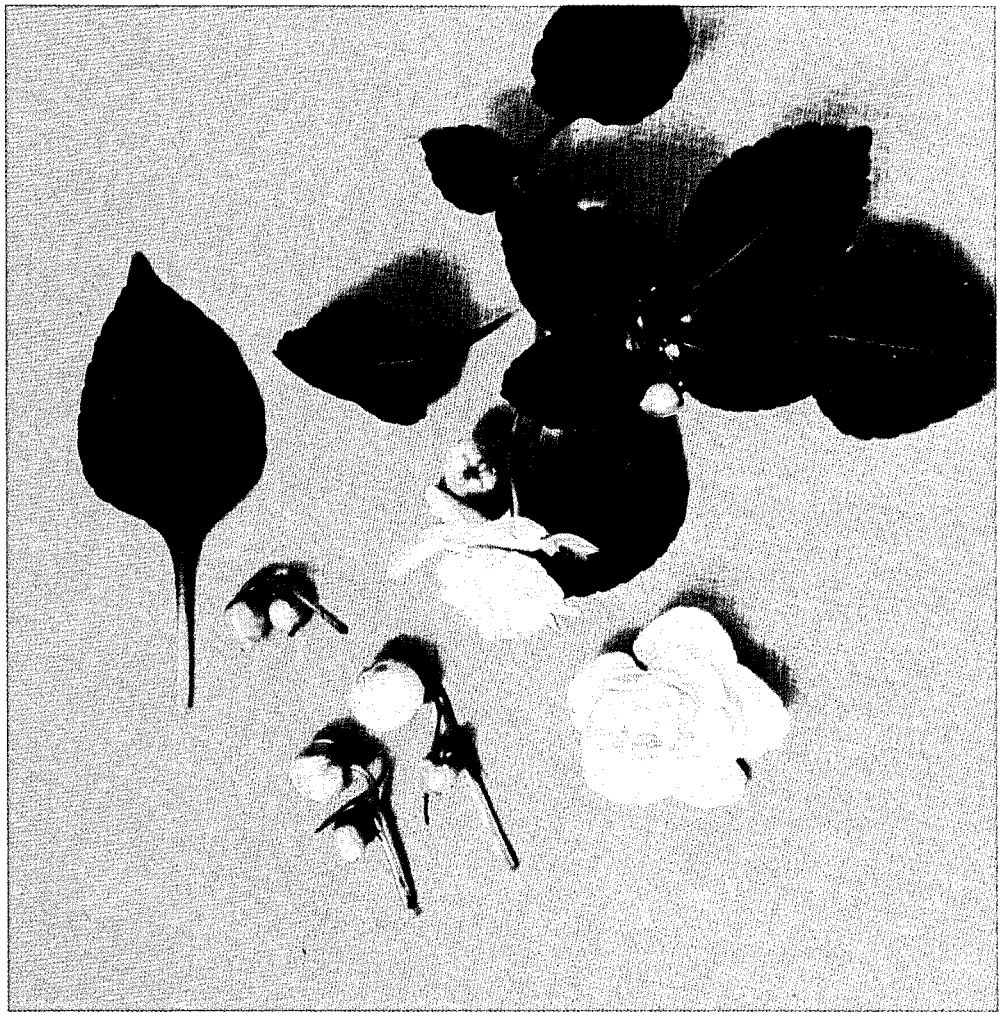
FIG. 2 is a close-up view illustrating the leaves, buds and flowers of the impatiens plant of the present invention.

Some of the leaves shown in FIG. 1 show a slight spotting. This spotting was caused by spraying with insecticide and is not normally characteristic of the leaves as will be apparent from examination of FIG. 2.

The new cultivar has flowers of larger diameter and much higher petal count (doubleness) and has a distinctively different shade of color than existing clones. Plants grow to a mature height of 45–55 cms. The description and drawings in this application were made from plants grown in one gallon containers inside a fiber-glass greenhouse with 15° C. minimum night temperatures and light shade (20%) at Gilroy, Calif., U.S.A. Color and size of plant parts vary slightly with different environmental conditions, but are uniform for similar aged plants in a similar environment. The following table compares the new cultivar with one of its parents.

TABLE OF COMPARISON

| | New cultivar | Appleblossom |
|---|---|---|
| Flower diameter | 30–40 mm | 25–35 mm. |
| Flower color, top of petals | Red 52C–D and 58D | Red 55D. |
| Flower color, bottom of petals | Red-purple 58D | Red 55D. |
| No. of whorls of petals | 6 to 12 | 3 to 4. |
| Flower spur length | 15 to 20 mm | 25 mm. |
| Flower spur color | Yellow-green 145A–D | Greyed-yellow 160C. |
| Leaf shape | Ovate | Ovate. |
| Leaf width | 30–40 mm | 35–40 mm. |
| Leaf length | 40–50 mm | 50–65 mm. |
| Leaf color top | Yellow-green 146B | Yellow-green 144A–146B. |
| Leaf color bottom | Yellow-green 147C–D | Yellow-green 148C–D. |

The blooming habit of the plant is recurrent and substantially continuous. The plant is generally bushy in shape and grows in a vigorous upright branching manner.

The new cultivar of the invention is of the genus Impatiens and the species *sultani* as are its parents.

That which is claimed is:

1. A new and distinctive cultivar of *Impatiens sultani,* substantially as herein shown and described, characterized particularly as to novelty by its large, highly double flowers and distinct light pink color.

No references cited.

ROBERT E. BAGWILL, Primary Examiner